US012733865B2

(12) United States Patent
Aslam et al.

(10) Patent No.: US 12,733,865 B2
(45) Date of Patent: Sep. 15, 2026

(54) SYSTEM AND A METHOD THEREOF FOR AUTOMATIC DETECTION OF EPILEPTOGENIC FOCUS IN PHARMACORESISTANT EPILEPSY

(71) Applicant: Amrita Vishwa Vidyapeetham, Tamil Nadu (IN)

(72) Inventors: Shameer Aslam, Uttarakhand (IN); Ashok Pillai, Kerala (IN); Siby Gopinath, Kerala (IN); Natesan Damodaran, Tamil Nadu (IN); Ramiah Rajeshkannan, Kerala (IN); Manjit Sarma, Kerala (IN)

(73) Assignee: Amrita Vishwa Vidyapeetham (IN)

( * ) Notice: Subject to any disclaimer, the term of this patent is extended or adjusted under 35 U.S.C. 154(b) by 95 days.

(21) Appl. No.: 18/794,994

(22) Filed: Aug. 5, 2024

(65) Prior Publication Data

US 2024/0398328 A1 Dec. 5, 2024

(30) Foreign Application Priority Data

Aug. 3, 2023 (IN) ............................ 202341052258

(51) Int. Cl.
*A61B 5/00* (2006.01)
*A61B 5/055* (2006.01)
(Continued)

(52) U.S. Cl.
CPC ............ *A61B 5/4094* (2013.01); *A61B 5/055* (2013.01); *G01R 33/4808* (2013.01);
(Continued)

(58) Field of Classification Search
CPC .................. A61B 5/4094; A61B 5/055; G01R 33/4808; G01R 33/481; G01T 1/2985;
(Continued)

(56) References Cited

PUBLICATIONS

Poirier, Stefan E., et al. "18F-FDG PET-guided diffusion tractography reveals white matter abnormalities around the epileptic focus in medically refractory epilepsy: implications for epilepsy surgical evaluation." European journal of hybrid imaging 4.1 (2020): 10. (Year: 2020).*

(Continued)

*Primary Examiner* — Keith M Raymond
*Assistant Examiner* — Johnathan Maynard
(74) *Attorney, Agent, or Firm* — Donald R. Boys; Central Coast Patent Agengy LLC

(57) ABSTRACT

The present invention introduces a system (S) and method for automatic detection of epileptogenic focus (EF) in pharmacoresistant epilepsy using an asymmetry index in FDG-PET images. The system (S) comprises of an acquisition unit for capturing FDG-PET scans and simultaneous whole-brain MRI images, a storage and communication unit for managing the acquired data, and a computation unit for processing and generating asymmetry index (AI) images. The method of the present invention comprises of a novel technique, PET asymmetry after anatomical symmetrization coregistered to MRI (PASCOM), to the AI images and is independent of healthy control PET data, facilitating implementation and multicenter translation. The method is effective in localizing the epileptogenic zone, especially in MRI-negative patient (Su), and can detect epileptogenic focus (EF) independently. This invention provides a reliable, cost-effective, and efficient method for detection of Epileptogenic focus (EF), assisting healthcare professionals in presurgical evaluation.

4 Claims, 8 Drawing Sheets

Flow chart of the working of system (PASCOM) of the invention A. Acquisition of PET and MRI Data, creation of flowfields .B. Advanced Processing of PET and MRI Data

(51) Int. Cl.
*A61N 5/10* (2006.01)
*G01R 33/48* (2006.01)
*G01T 1/29* (2006.01)
*G16H 30/40* (2018.01)
*G16H 40/67* (2018.01)

(52) U.S. Cl.
CPC .......... *G01R 33/481* (2013.01); *G01T 1/2985* (2013.01); *G16H 30/40* (2018.01); *G16H 40/67* (2018.01); *A61N 2005/1052* (2013.01); *G06T 2207/10104* (2013.01)

(58) Field of Classification Search
CPC .................. G16H 30/40; G16H 40/67; A61N 2005/1052; G06T 2207/10104
See application file for complete search history.

(56) References Cited

PUBLICATIONS

Siemens. "Biograph mMR." 2011 retrieved from marketing.webassets.siemens-healthineers.com/1800000000082895/ce5836403cd9/MRI-Biograph-mMR-Product_Brochure_1800000000082895.pdf (Year: 2011).*

Kim, J. S., Cho, H., Choi, J. Y., Lee, S. H., Ryu, Y. H., Lyoo, C. H., & Lee, M. S. (2015). Feasibility of computed tomography-guided methods for spatial normalization of dopamine transporter positron emission tomography image. PLoS One, 10(7), e0132585. (Year : 2015).*

The Wellcome Centre for Human Neuroimaging. "SPM 12—Statistical Parametric Mapping." Jul. 2023 (Year: 2023).*

Aslam, S., Damodaran, N., Rajeshkannan, R., Sarma, M., Gopinath, S., & Pillai, A. (2022). Asymmetry index in anatomically symmetrized FDG-PET for improved epileptogenic focus detection in pharmacoresistant epilepsy. Journal of neurosurgery, 138(3), 828-836. (Year: 2022).*

Shang, K., Wang, J., Fan, X., Cui, B., Ma, J., Yang, H., . . . & Lu, J. (2018). Clinical value of hybrid TOF-PET/MR imaging-based multiparametric imaging in localizing seizure focus in patients with MRI-negative temporal lobe epilepsy. American Journal of Neuroradiology, 39(10), 1791-1798. (Year: 2018).*

Galazzo, Ilaria Boscolo, et al. "Cerebral metabolism and perfusion in MR-negative individuals with refractory focal epilepsy assessed by simultaneous acquisition of 18F-FDG Pet and arterial spin labeling." NeuroImage: Clinical 11 (2016): 648-657. (Year: 2016).*

Siemens. "Biograph mMR." 2021 retrieved from siemens-healthineers.com/en-us/magnetic-resonance-imaging/mr-pet-scanner/biograph-mmr (Year: 2021).*

Didelot, Adrien, et al. "Voxel-based analysis of asymmetry index maps increases the specificity of 18F-MPPF PET abnormalities for localizing the epileptogenic zone in temporal lobe epilepsies." Journal of Nuclear Medicine 51.11 (2010): 1732-1739. (Year: 2010).*

Aslam, S., Rajeshkannan, R., Sandya, C. J., Sarma, M., Gopinath, S., & Pillai, A. (Jul. 2022). Statistical asymmetry analysis of volumetric MRI and FDG PET in temporal lobe epilepsy. Epilepsy & Behavior, 134, 108810. (Year: 2022).*

Li, C., Chen, W., Li, X., Li, T., Chen, Y., Zhang, C., . . . & Wang, X. (2023). Gray matter asymmetry atypical patterns in subgrouping minors with autism based on core symptoms. Frontiers in Neuroscience, 16, 1077908. (Year: 2023).*

Floris, D. L., Lai, M. C., Auer, T., Lombardo, M. V., Ecker, C., Chakrabarti, B., . . . & Suckling, J. (2016). Atypically rightward cerebral asymmetry in male adults with autism stratifies individuals with and without language delay. Human brain mapping, 37(1), 230-253. (Year: 2016).*

Pizzagalli, F. (2012). Etude par neuroimagerie IRM de la représentation centrale des mouvements de la main chez les sujets sains et chez les patients après chirurgie de la main (Doctoral dissertation, Université de Grenoble). (Year: 2012).*

Kim, J. S., Koo, D. L., Joo, E. Y., Kim, S. T., Seo, D. W., & Hong, S. B. (2016). Asymmetric gray matter vol. changes associated with epilepsy duration and seizure frequency in temporal-lobe-epilepsy patients with favorable surgical outcome. Journal of Clinical Neurology, 12(3), 323-331. (Year: 2016).*

Soma, T., Momose, T., Takahashi, M., Koyama, K., Kawai, K., Murase, K., & Ohtomo, K. (2012). Usefulness of extent analysis for statistical parametric mapping with asymmetry index using interictal FGD-PET in mesial temporal lobe epilepsy. Annals of nuclear medicine, 26(4), 319-326. (Year: 2012).*

Poirier, S. E. (2020). A Hybrid PET/MRI Brain Connectivity Approach for Improving Epilepsy Surgical Evaluation (Master's thesis, The University of Western Ontario (Canada)). (Year: 2020).*

The Wellcome Centre for Human Neuroimaging. "SPM12 Manual." 2021 retrieved from www.fil.ion.ucl.ac.uk/spm/doc/manual.pdf (Year: 2021).*

* cited by examiner

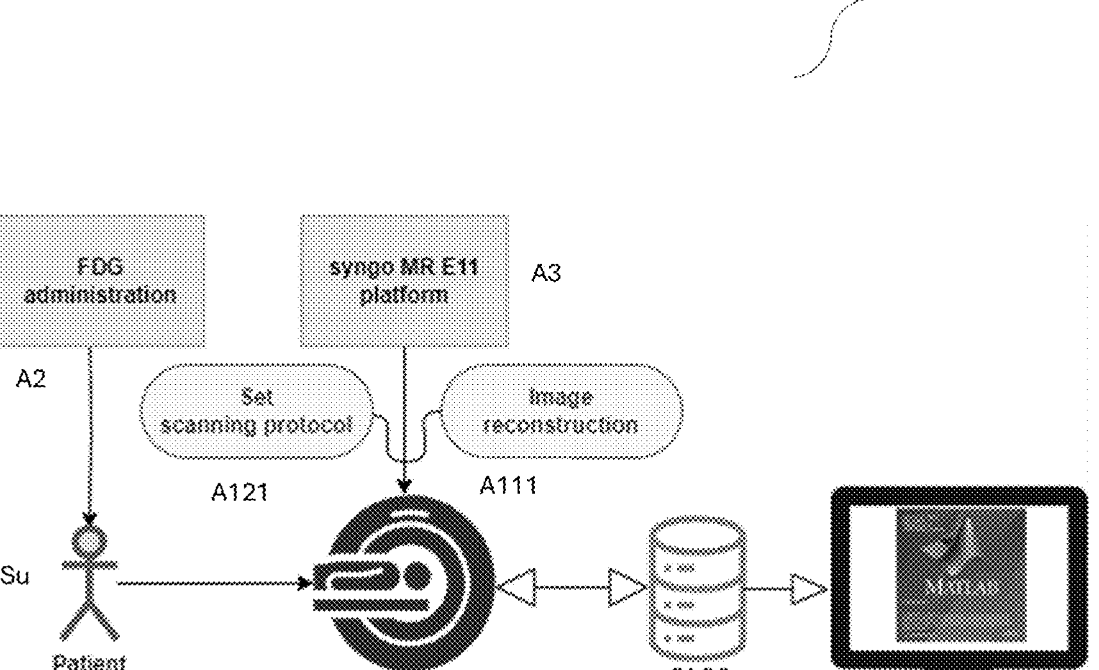
Figure 1: Overview of the system (PASCOM) of the invention.

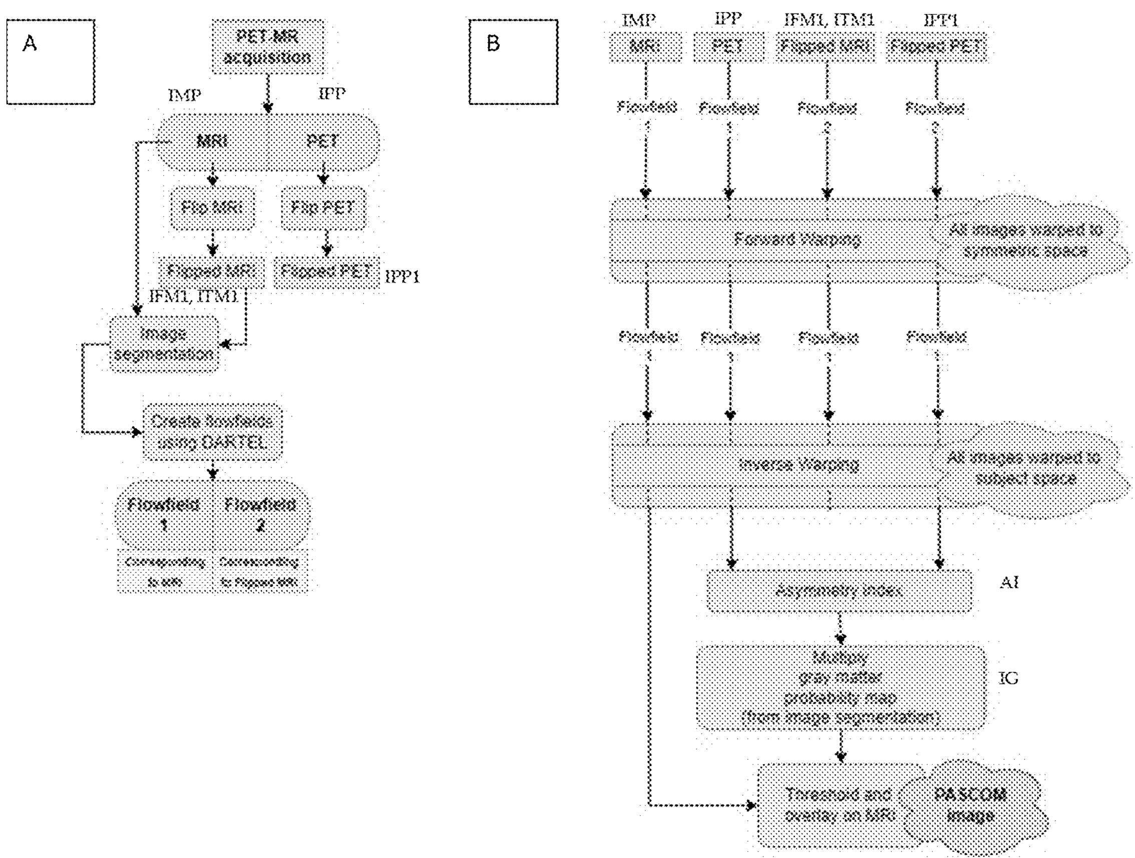
Figure 2: Flow chart of the working of system (PASCOM) of the invention A. Acquisition of PET and MRI Data, creation of flowfields .B. Advanced Processing of PET and MRI Data

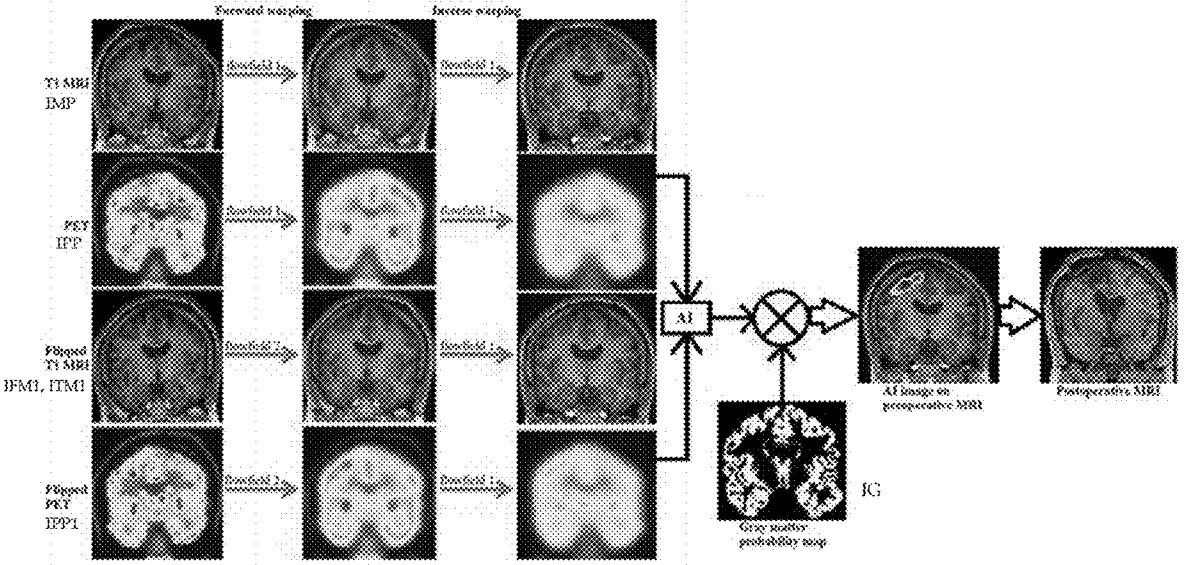
Figure 3: PASCOM technique to create the AI image of FDG-PET with the resultant hypometabolism overlaid on preoperative MR image.

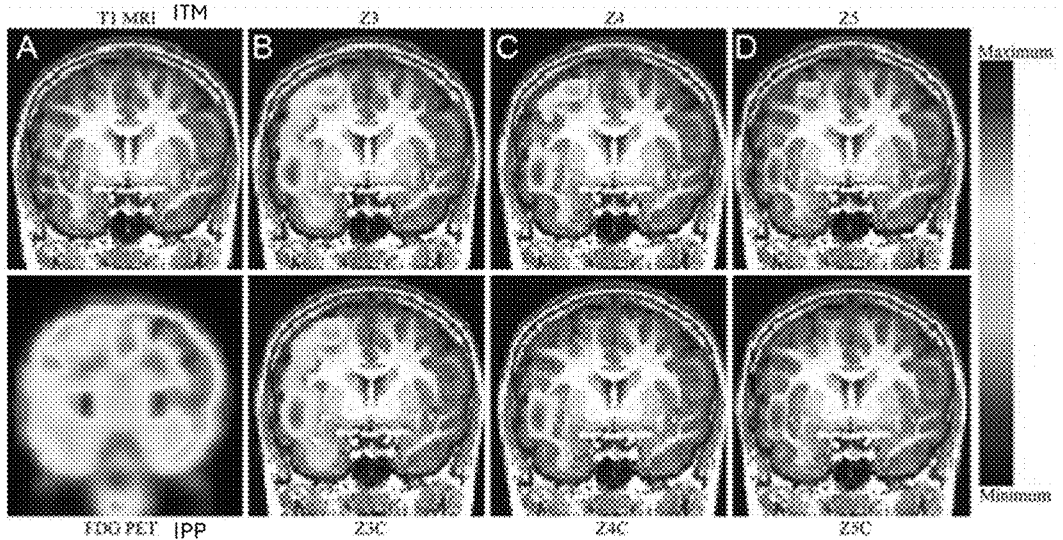
Figure 4: Threshold and cluster AI images. T1-weighted MRI (A) and FDG-PET (B) AI images thresholded at z > 3 and clustered; (C) AI images thresholded at z > 4 and clustered; and (D) AI images thresholded at z > 5 and clustered.

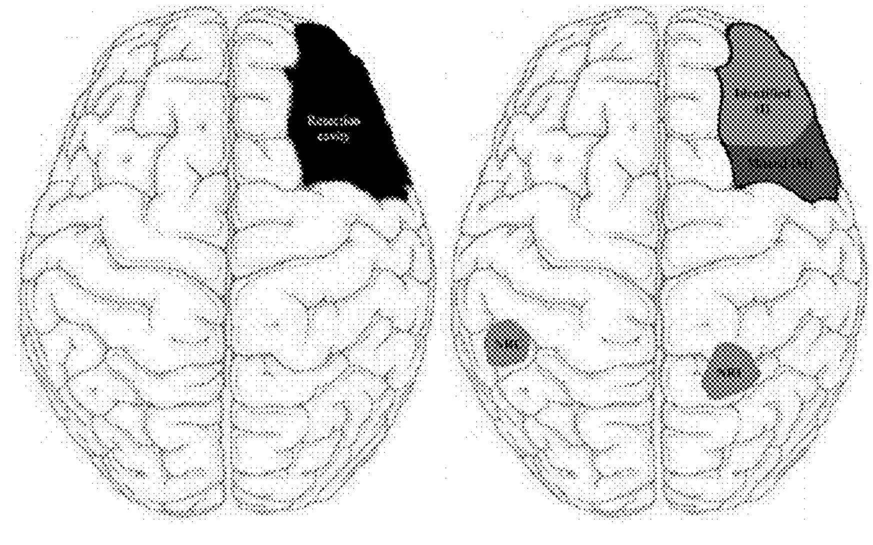
Figure 5: Analysis parameters: resection cavity (left) and I, M, NRI, and NRC (right). The detected FDG-PET hypometabolism appears in green, and the nonhypometabolic resected region appears in red.

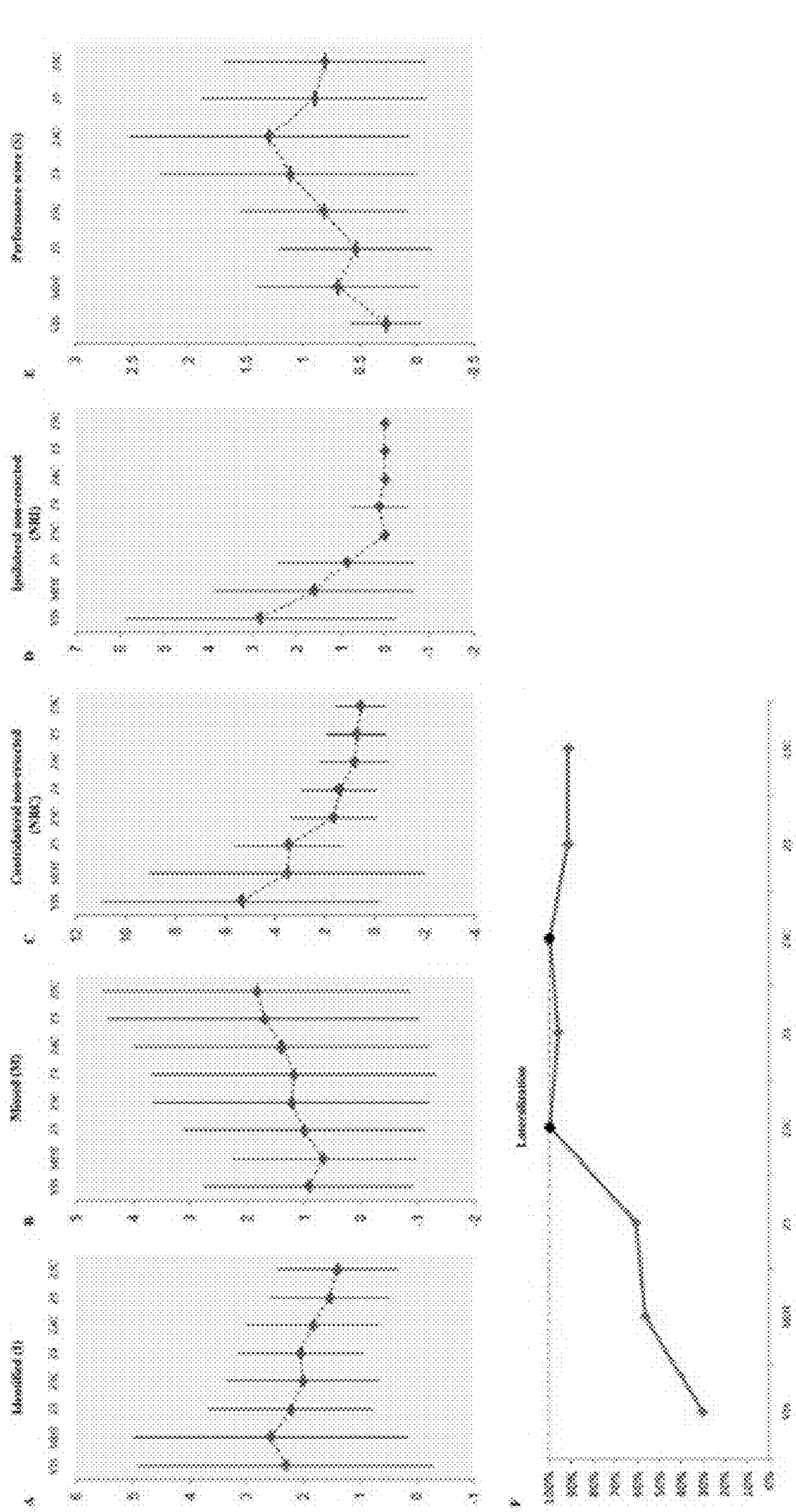
Figure 6 : Descriptive mean and standard deviation of analysis parameters along with the lateralization of epileptogenicity.

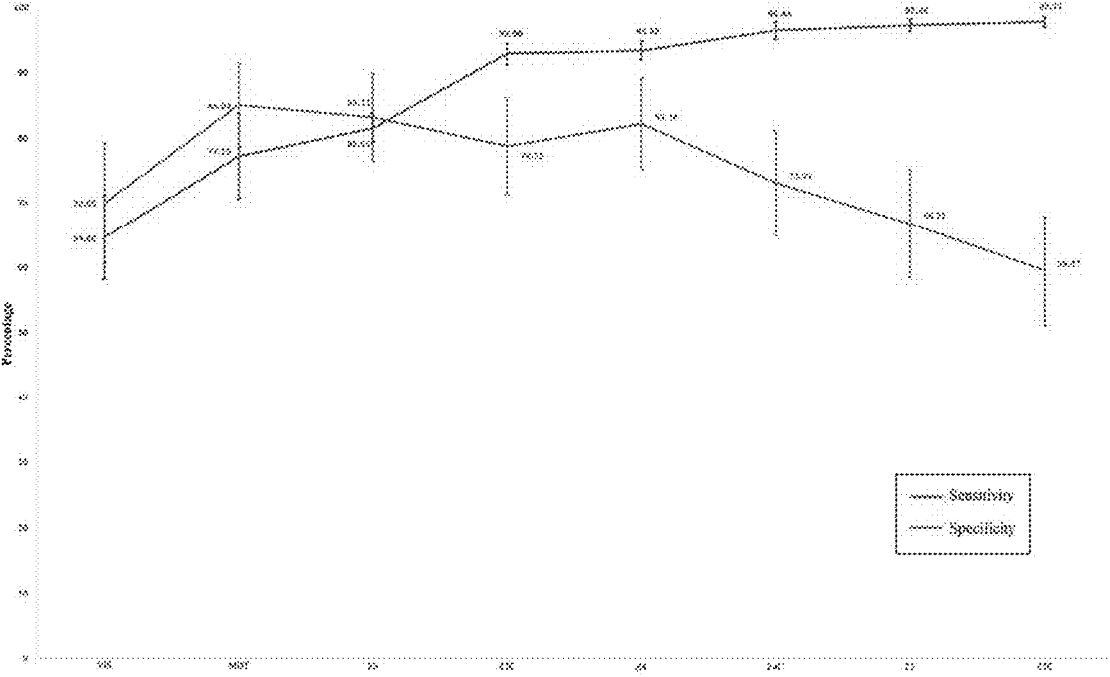
Figure 7: Sensitivity and specificity for each FDG-PET analysis technique is labeled, with the error bars representing the standard errors.

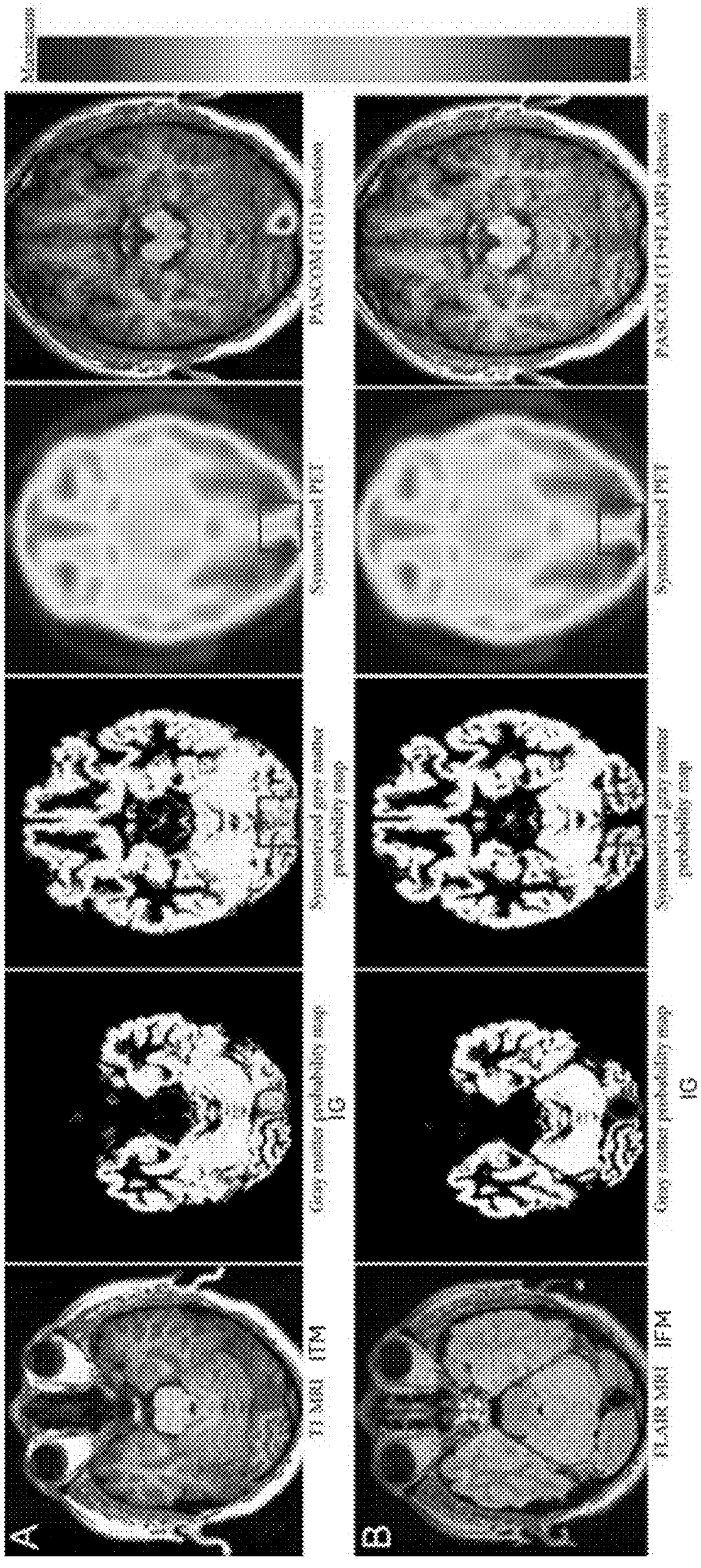
Figure 8: FDG-PET asymmetry detection with and without using FLAIR MRI.

SYSTEM AND A METHOD THEREOF FOR AUTOMATIC DETECTION OF EPILEPTOGENIC FOCUS IN PHARMACORESISTANT EPILEPSY

CROSS REFERENCE TO RELATED APPLICATIONS

The present application claims priority to India Patent Application 202341052258 filed 3 Aug. 2023. All disclosure of the parent case is incorporated herein at least by reference.

BACKGROUND OF THE INVENTION

1. Field of the Invention

The present invention is in the technical field of medical diagnostic procedures and relates more specifically to detection of epileptogenic focus in harmacoresistant epilepsy.

2. Description of Related Art

Epilepsy is a chronic noncommunicable disease of the brain that affects humans of all ages. It is also known as a "seizure disorder", a brain disorder that is characterized by recurrent seizures, which are short-term episodes of involuntary movement that may involve a part of the body (partial) or the entire body (generalized) of human subject and are sometimes accompanied by loss of consciousness and control of bowel or bladder function. Around fifty million people worldwide have epilepsy, making it one of the most common neurological diseases globally.

Human subjects with epilepsy whose seizures do not successfully respond to antiseizure medication therapy are considered to have pharmacoresistant epilepsy. This condition is also referred to as intractable, medically refractory, or drug-resistant epilepsy (DRE). Drug-resistant epilepsy has a number of negative consequences like learning and development problems in children, epilepsy-related injury, increased risk of sudden unexpected death in epilepsy (SUDEP), increased risk of emotional and behavioral problems, poorer occupational outcomes, increased risk of side effects to multiple antiseizure medications etc.

Epileptogenic zone is a theoretical concept that is defined as the area of cortex indispensable for the generation of clinical seizures. The epileptogenic focus is the site in the brain from which the seizure originated and is most likely equivalent to the epileptogenic zone. Modern epileptologists use a variety of diagnostic tools, such as analysis of seizure semiology, electrophysiological recordings, functional testing and neuroimaging techniques to define the location and boundaries of the epileptogenic zone. The ability to define the epileptogenic zone precisely is essentially a function of the sensitivities and specificities of the diagnostic methods.

Several studies have shown that one of the main treatment options in drug resistant epilepsy is Resective surgical therapy that has the potential to eliminate seizures in many patients with localization-related drug resistant epilepsy (DRE). However, for a patient to be a good candidate for surgery, one of the primary conditions to be met is that the area of the brain where seizures originate is clearly identified.

A number of literatures have been published including patents and non-patent documents in said domain.

Drug-resistant epilepsy is a diagnostic and therapeutic challenge, mainly in patients with negative magnetic resonance imaging (MRI) findings. The margins of resection are determined by the findings of intracranial EEG (either SEEG and/or acute ECoG) with or without anatomical borders of a lesion as defined on structural MRI. However as per a non-patent literature titled "Epileptogenic zone detection in MRI negative epilepsy using adaptive thresholding of arterial spin labeling data", by Martin Gajdoš, Pavel Řiha, Martin Kojan, Irena Doležalová, Henk J. M. M. Mutsaerts, Jan Petr and Ivan Rektor, published in 2021, no identifiable epileptogenic lesion is found in 20% to 40% of epilepsy surgery candidates using the anatomical MRI that is part of the standard presurgical MRI protocol. Therefore, it is necessary to extend the imaging in these cases with other techniques like PET, measuring the physiology and pathophysiology of the brain, to facilitate localization of an epileptogenic focus where MRI fails.

As per a non-patent literature titled "Presurgical evaluation of epilepsy" by Rosenow F and Lüders H., published in "Brain", 2001, the postoperative outcome in drug-resistant epilepsy patients who are candidates for resective surgery heavily relies on the presurgical workup. The region of hypometabolism on interictal fluorine 18-labeled fluorodeoxyglucose positron emission tomography (FDG-PET) is an established biomarker for localization of the epileptogenic zone (EZ) equivalent to epileptogenic focus. Therefore, there is a requirement for rigorous evaluation of FDG-PET that would assist to construct a precise hypothesis on the EZ.

Conventionally, interictal FDG-PET images are visually evaluated by appreciating the interhemispheric metabolic asymmetry to localize hypometabolism. The visual analysis of FDG-PET can however vary depending on the expertise of the clinician and interrater reliability.

Several previous studies have shown that computer-aided PET analysis techniques may outperform visual analysis. However, these techniques had a drawback that no anatomical correction was done prior to calculating AI images. The Montreal Neurological Institute (MNI) space, though standardized, has interhemispheric structural asymmetry. A patent document, CN112927187A, titled "Method for automatically identifying and positioning focal cortical dysplasia epileptic focus", dated 27 Jan. 2021, brings out that improvement of diagnosis rate is one of the most important challenges of current epileptic surgery, and the current clinical main diagnosis methods depends on artificial visual interpretation and has the defects of low result accuracy, strong experience dependence etc. Therefore, there is a need for standardization and mathematical precision using automation in the analysis of PET images to provide analysis that is accurate and experience independent to aid in better presurgical outcomes.

Though grossly symmetrical, the fine cortical gyral and sulcal anatomy of the brain is significantly asymmetrical across the midsagittal plane. Moreover, in many patients with epilepsy, pathological cortical atrophy may further add to the asymmetry. Some previous studies include a non-patent literature titled, "Statistical parametric mapping of regional glucose metabolism in mesial temporal lobe epilepsy" by Van Bogaert P, Massager N, Tugendhaft P, et al, published in Neuroimage. 2000, have used the intensity values of interhemispheric pairs of PET voxels to calculate voxel-based Asymmetry Index (AI). However, it is seen that interhemispheric asymmetry tends to reduce the accuracy of the AI measurement.

Numerous studies have checked the asymmetry of PET images roughly by spatially transforming the PET data to standard Montreal Neurological Institute (MNI) space. A non-patent literature titled, "Voxel-based comparison of preoperative FDG-PET between mesial temporal lobe epilepsy patients with and without postoperative seizure-free outcomes" by Takahashi M, Soma T, Kawai K, Koyama K, Ohtomo K, Momose T, published in 2012, has used a more sophisticated method by creating the symmetrical PET template from their in-house PET template to transform individual PET images to a symmetrical space. Hence, there is a drawback in these approaches that the utilization of symmetrical PET template may introduce artificial symmetry or misalignments by mirroring the interhemispheric metabolism, ignoring the existing structural asymmetry. Also, the methodology was limited to evaluating temporal lobe epilepsy patients only because of midline artifacts over the midsagittal plane introduced while creating the symmetrical template using PET data.

The FDG-PET analysis in epilepsy predominantly relies on interhemispheric metabolic asymmetry detection. Several studies including a non-patent literature titled "Usefulness of extent analysis for statistical parametric mapping with asymmetry index using inter-ictal FGD-PET in mesial temporal lobe epilepsy", by Soma T, Momose T, Takahashi M, et al., published in Ann Nucl Med. in 2012, have utilized the asymmetry index (AI) measure to quantify this asymmetry. There are different methodologies to appreciate interhemispheric metabolic asymmetry, ranging from manually marking the region of interest to overlaying anatomical atlases onto PET images to assess the mean metabolism value on each side of the brain PET. However, it is seen that when interhemispheric hypometabolism asymmetry index (AI) is used to identify the EZ, it may lead to false localization in AI images due to non-congruent regions without interhemispheric anatomical symmetrization.

A non-patent literature titled, "(18)F-FDG PET in localization of frontal lobe epilepsy: comparison of visual and SPM analysis", by Kim Y K, Lee D S, Lee S K, Chung C K, Chung J K, Lee M C, published in 2002, describes a PET analysis based on a statistical comparison of a patient's PET scans to healthy control PET scans. Unlike MRI, which does not require radioactive tracer injection, collecting age- and gender-matched normative PET data from healthy volunteers is difficult. Therefore, there is a sizable drawback in these methods in prior arts due to a dependence on normative control PET data making it difficult for many clinical centers to widely adopt these techniques. Furthermore, the unavailability of age-matched normative PET data for pediatric epilepsy patients restricted the PET evaluation to visual analysis.

Therefore, there is a need for a system and a method thereof for automatic detection of epileptogenic focus in pharmacoresistant epilepsy that is easy to implement, experience independent and cost effective in providing an accurate, reliable, precise, presurgical evaluation with complete coverage of the brain of the subject.

OBJECTS OF THE INVENTION

In order to overcome the shortcomings in the existing state of the art, an important object of the present invention is to provide a system for automatic detection of epileptogenic focus in pharmacoresistant epilepsy using asymmetry index in FDG-PET images for aiding in presurgical evaluation.

Another object of the invention is to provide a method for automatic detection of epileptogenic focus in pharmacoresistant epilepsy using asymmetry index in FDG-PET images for aiding in presurgical evaluation.

Yet another object of the present invention is to provide a method of PET asymmetry after anatomical symmetrization coregistered to MRI (PASCOM), utilizing interhemispheric metabolic asymmetry on interictal FDG-PET images to localize the epileptogenic zone in pharmacoresistant epilepsy.

Yet another object of the present invention is to provide a system for automatic detection of epileptogenic focus in pharmacoresistant epilepsy that is capable of whole-brain FDG-PET analysis to quantify interhemispheric metabolic asymmetry for localizing focal hypometabolism.

Yet another object of the present invention is to provide a method for automatic detection of epileptogenic focus in pharmacoresistant epilepsy that is effective in localization of an epileptogenic focus even in MRI negative subjects.

Yet another object of the present invention is to provide a system capable of creating an effective symmetrical template before analyzing the whole-brain PET to avoid the issues of misalignments or artificial asymmetry for detection of epileptogenic focus in pharmacoresistant epilepsy using asymmetry index in FDG-PET images.

Yet another object of the present invention is to provide a system capable of detecting epileptogenic focus in pharmacoresistant epilepsy independently without the requirement of corroboration with any other clinical data.

Yet another object of the present invention is to provide a system for automatic detection of epileptogenic focus in pharmacoresistant epilepsy using FDG-PET that is independent of control PET data making it easy to implement the evaluation of the AI images and is convenient for multicenter translation.

Yet another object of the present invention is to provide a method for automatic detection of epileptogenic focus in pharmacoresistant epilepsy using FDG-PET images that overcomes the challenge due to structural asymmetry in the conventional methods of analysis.

Yet another object of the present invention is to provide a system and a method thereof for automatic detection of epileptogenic focus in pharmacoresistant epilepsy that is less time consuming, reliable, cost effective, efficient and therefore economically significant in identification of epileptogenic focus for a better presurgical evaluation.

BRIEF SUMMARY OF THE INVENTION

Accordingly, the present invention discloses a system and a method thereof for automatic detection of epileptogenic focus in pharmacoresistant epilepsy using asymmetry index in FDG-PET images. This system utilizes interhemispheric metabolic asymmetry on interictal FDG-PET images to localize the epileptogenic zone by identifying the hypometabolic cerebral cortex that would assist healthcare professionals in presurgical evaluation in pharmacoresistant epilepsy.

The system and the method of the invention discloses an automated FDG-PET analysis technique of PET asymmetry after anatomical symmetrization coregistered to MRI (PASCOM) to enhance visual analysis. This technique is based on the calculation of an interhemispheric metabolism AI following the voxel-based correction of interhemispheric anatomical asymmetry. PASCOM is a non-statistical technique, thus independent of healthy control PET data that was validated through the Engel class I postsurgical outcomes. Hence, this system has the advantage of overcoming the challenges of unavailability of normative PET data, making it easier to implement the evaluation of the AI images and is and convenient for multicenter translation.

The system of the present invention comprises of but is not limited to an acquisition unit, a processing unit etc. The acquisition unit involves interictal FDG-PET acquired on PET/MR systems such as a Seimens Biograph mMR using imaging platforms such as syngo MR E11 platform following the intravenous injection of 18F FDG tracer. The system works on acquired data that has undergone iterative reconstruction of the PET data with a multiple number of iterations and subsets. The system enables simultaneous acquisition of whole brain 3D FLAIR and 3D T1 weighted MRI with high resolution such as 1 mm isovolumetric voxel in the sagittal plane. The processing unit involves a high end windows computer with fast core such as core i7 processor and a high capacity RAM such as 16 GB RAM. The system utilizes coding programming platforms such as MATLAB version R2017b.

The method of present invention broadly comprises of steps of but not limited to data acquisition, data processing, creation of threshold and cluster AI images etc. Data acquisition comprises of but not limited to acquiring FDG PET scans along with simultaneous whole-brain MRI images such as 3D FLAIR or 3D T1-weighted sequences MRI images. The data processing comprises of but is not limited to coregistering of the PET scans and MRI such as FLAIR MRI to the other images such as T1-weighted sequence MRI followed by flipping and such other steps of image processing. Image processing such as multispectral segmentation is carried out to create the gray and white matter probability maps along with import files such as DARTEL import files in programming platforms such as MATLAB. Data processing also includes the creation of symmetrical template using sources and tools such as DARTEL import files for nonlinear registration for forward warping of the images to common space, inverse warping that allows inverse transformation of deformed images back to the subject space after computing AI image etc. Detection of hypometabolism is done after a few other steps of image processing and the AI is determined.

In the technique of the present invention, PASCOM, the misalignments due to symmetrization are avoided by creating patient specific symmetrical template by nonlinearly coregistring the flipped and unflipped images rather than taking the average of the asymmetries. It also allows inverse conversion of symmetricized PET images back to the subject space to map the significant metabolic asymmetry on the non-deformed patient brain.

The system of the present invention uses tools such as DARTEL to create the symmetrical anatomical template from individual MRI studies to fix the structural asymmetry. It uses the individual structural MRI to create the patient specific symmetrical templates irrespective of metabolic asymmetry in PET data. It also allows reliable overlap of interhemispheric structures before calculating AI images. Thus, the system of the invention avoids misalignments due to symmetrization and therefore, could be used for extratemporal epilepsy evaluation.

The automated technique of the present invention facilitates standardization and mathematical precision to the analysis of PET compared to visual interpretation. The system and the method of the invention are particularly effective in aiding in localization of the EZ, especially in MRI-negative patients. The system is capable of detecting epileptogenic focus in pharmacoresistant epilepsy independently without the requirement of corroboration with any other clinical data.

Accordingly, the present invention provides a system and a method thereof for automatic detection of epileptogenic focus in pharmacoresistant epilepsy using asymmetry index in FDG-PET images, that is less time consuming, reliable, cost effective, efficient and therefore economically significant in detection of epileptogenic focus for assisting healthcare professionals in presurgical evaluation.

BRIEF DESCRIPTION OF THE SEVERAL VIEWS OF THE DRAWINGS

FIG. 1 displays an overview of the system (PASCOM) of the invention.

FIG. 2 displays a flow chart of the working of system (PASCOM) of the invention.

FIG. 3 displays a technique called PACOM to create an AI image of FDG-PET with resultant hypometabolism overlaid on a preoperative MR image.

FIG. 4 displays threshold and cluster AI images.

FIG. 5 displays analysis parameters: resection cavity (left) and I, M, NRI, and NRC (right).

FIG. 6 displays a descriptive mean and standard deviation of analysis parameters along with S and the lateralization of epileptogenicity.

FIG. 7 displays sensitivity and specificity for each FDG-PET analysis technique labeled, with error bars representing the standard errors.

FIG. 8 displays FDG-PET asymmetry detection with and without using FLAIR MRI.

DETAILED DESCRIPTION OF THE INVENTION

While the invention has been disclosed with reference to certain embodiments, it will be understood by those skilled in the art that various changes may be made, and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a" "an", and "the" include plural references. Additionally, a reference to the singular includes a reference to the plural unless otherwise stated or inconsistent with the disclosure herein.

Unless otherwise defined, all technical and scientific terms used herein have the same meaning as commonly understood by those skilled in the art to which this disclosure belongs. The system, methods, and examples provided herein are only illustrative and not intended to be limiting.

The abbreviations used in the invention are represented in table 1 as below:

TABLE 1

Legend of abbreviations

| S. no. | Particulars | Legend |
|---|---|---|
| 1 | Asymmetry index | AI |
| 2 | PET asymmetry after anatomical symmetrization coregistered to MRI | PASCOM |
| 3 | Positron emission tomography | PET |
| 4 | Magnetic resonance imaging | MRI |
| 5 | Fluorodeoxyglucose positron emission tomography | FDG-PET |
| 6 | Epileptogenic zone | EZ |
| 7 | Multidisciplinary team discussion | MDT |
| 8 | Fluid-attenuated inversion recovery-MRI | FLAIR MRI |

TABLE 1-continued

| Legend of abbreviations | | |
|---|---|---|
| S. no. | Particulars | Legend |
| 9 | Full width at half maximum; | FWHM |
| 10 | Diffeomorphic Anatomical Registration Through Exponentiated Lie Algebra | DARTEL |
| 11 | Visual analysis by nuclear medicine consultant blinded to clinical data | VIS |
| 12 | Electrocorticography | ECOG |
| 13 | Identified region | I |
| 14 | Missed region | M |
| 15 | Non-resected region | NR |
| 16 | NR, contralateral | NRC |
| 17 | NR, ipsilateral | NRI |
| 18 | Performance score | Sc |
| 19 | Stereo-EEG | SEEG |
| 20 | Video-EEG | VEEG |
| 21 | Basic pulse sequence parameters: Repetition time | TR |
| 22 | Echo time | TE |
| 23 | Inversion time | TI |
| 24 | Field of View | FOV |
| 25 | Number of excitations | NEX |

Some of the technical terms used in the specification are elaborated as below:

Epilepsy: Epilepsy also known as “seizure disorder” is a chronic noncommunicable disease of the brain that affects people of all ages. It is also known disorder that is characterized by recurrent seizures, which are short-term episodes of involuntary movement that may involve a part of the body (partial) or the entire body (generalized) and are sometimes accompanied by loss of consciousness and control of bowel or bladder function.

Pharmacoresistant epilepsy or Drug resistant epilepsy: Patients with epilepsy whose seizures do not successfully respond to antiseizure medication therapy are considered to have pharmacoresistant epilepsy also known as drug-resistant epilepsy (DRE).

Epileptic zone: Epileptic zone is defined as the area of cortex that is necessary and sufficient for initiating seizures and whose removal (or disconnection) is necessary for complete abolition of seizures in epilepsy.

Epileptogenic focus: The epileptogenic focus or seizure focus is the site in the brain from which the seizure originated and is most likely equivalent to the epileptogenic zone.

Asymmetry index: The asymmetry index is the ratio of the skewness to the standard error. It is an indication of the asymmetry of a distribution. Brain asymmetry can be defined as a characteristic and/or property that differs between hemispheres, either at structural or at functional levels.

Hypometabolism: Hypometabolism is defined as the physiological state of having decreased metabolic rate, which is abnormal. The extent of uptake is viewed in different colors in PET scan. If the brain glucose uptake is decreased due to some reason, it is called hypometabolic state of brain. Hypometabolism is a common finding or feature of most neurodegenerative disorders.

Interictal: It denotes the phase occurring between seizures as of epilepsy.

Engel class I postsurgical outcome: Numerous classification systems are used by epilepsy centers to indicate the outcome of surgery, wherein the Engel classification system is the most commonly used scale. The Engel Class 1 classification means the patient is free of disabling seizures (completely seizure free; nondisabling, simple partial seizures only; some disabling seizures, but free of disabling seizures for at least 2 years; generalized convulsion with antiepileptic drug withdrawal only).

Subjects—A patient, person, or organism that is the object of research, treatment, experimentation, or dissection. Here in the description the term subjects include humans or animals who have been researched upon for screening, prediction and detection of medical conditions such as epilepsy. The term includes the patients who undergo tests or any screening for epilepsy.

The reference numerals used in the present invention are tabulated below in table 2.

TABLE 2

| Legend of Reference numerals | | |
|---|---|---|
| Ser No. | Item description | Reference signs/ numerals |
| 1 | System | S |
| 2 | Subject/Patient | Su |
| 3 | Epileptogenic focus | EF |
| 4 | Acquisition module | A |
| | Acquisition submodule or medical hardware system | A1 |
| | PET detector | A11 |
| | Image Reconstruction submodule | A111 |
| | MRI scanner | A12 |
| | MRI Sequences Software/tool | A121 |
| | Injection unit | A2 |
| | System software/tool | A3 |
| 5 | Storage and communication module/PACS module | SC |
| | Storage device | SC1 |
| | processor | SC3 |
| 6 | Computation Module | C |
| | Computing submodule | C1 |
| | PASCOM/Processing submodule | C2 |
| | Storage device | C3 |
| | MATLAB/language and interactive tool | C4 |
| | SPM 12 toolbox/toolbox | C5 |
| | Processor | C6 |
| | Computing tool for image registration/DARTEL | C7 |
| | Smoothing tool | C8 |
| 7 | Image Processing | Ip |
| | MRI data/scan/image | IM |
| | FLAIR MRI image/data | IFM |
| | T1 MRI image/T1-weighted MRI | ITM |
| | Pre-processed MRI data/image | IMP |
| | PET scan/data/image | IP |
| | Pre-processed PET data/image | IPP |
| | Co-registered image | IC |
| | Flipped T1 MRI image | ITM1 |
| | Flipped FLAIR MRI image | IFM1 |
| | Flipped PET image | IPP1 |
| | Warped un-flipped PET image | IPPW |
| | Warped flipped PET image | IPP1W |
| | Warped un-flipped TI MRI image | ITMW |
| | Warped flipped TI MRI image | ITM1W |
| | grey and white matter probability maps | IG |
| | Symmetrical template | IT |

The present invention discloses a system (S) and a method thereof for automatic detection of epileptogenic focus (EF) in pharmacoresistant epilepsy using asymmetry index in FDG-PET images. This system (S) utilizes interhemispheric metabolic asymmetry on interictal FDG-PET images to localize the epileptogenic zone by identifying the hypometabolic cerebral cortex that would assist healthcare professionals in presurgical evaluation in pharmacoresistant epilepsy.

In drug-resistant epilepsy patients who are candidates for resective surgery, the postoperative outcome heavily relies on the presurgical workup. Positron emission tomography (PET) imaging has an essential role in the presurgical evaluation of epileptogenic foci in drug-resistant epilepsy by identifying the hypometabolic cerebral cortex.

The system (S) and method of the present invention employ an automated FDG-PET analysis technique, termed PET asymmetry after anatomical symmetrization co-registered to MRI (PASCOM), to enhance visual analysis. The PASCOM technique is based on the calculation of an interhemispheric metabolism parameter called asymmetry index (AI) following the voxel-based correction of interhemispheric anatomical asymmetry on interictal fluorine 18-labeled fluorodeoxyglucose (FDG)-PET to better localize the epileptogenic zone. For this the system (S) requires simultaneous acquisition of PET imaging and whole brain 3D FLAIR and 3D T1 weighted MRI with high resolution isovolumetric voxel in the sagittal plane. This technique is independent of healthy control PET data, which makes it easier to implement.

The system (S) and the method thereof for automatic detection of epileptogenic focus (EF) in pharmacoresistant epilepsy using asymmetry index in FDG-PET images is as described below.

As per an embodiment of the invention an overview of the system (S) is depicted in FIG. 1. The system (S) of the present invention for automatic detection of epileptogenic focus (EF) in pharmacoresistant epilepsy comprises of three key components. The first component of the system (S) is an acquisition module (A) comprising of one acquisition submodule (A1) that is a medical hardware system (A1) comprising of PET detector (A11) and MRI scanner (A12) for acquiring and pre-processing of inputs in the form of PET data (IP) and MRI data (IM) of said subjects (Su), one injection unit (A2) for intravenous administration of radiotracer such as but not limited to Fluorodeoxyglucose (FDG) for PET scanning and one tool (A3) that controls the operation of the MRI scanner (A12) to include the initiation of sequences, data acquisition parameters and integration with the PET detector (A11).

The second component is a storage and communication module (SC) that is a medical imaging technology used for storing, retrieving, presenting, and sharing or communicating the preprocessed PET (IPP) and MRI data (IMP) from acquisition module (A).

Another component of the system (S) is a computation module (C) for accessing the pre-processed PET (IPP) and MRI data (IMP) from the storage and communication module (SC) and performing advance processing of the pre-processed PET (IPP) and MRI data (IMP) to localize epileptogenic focus (EF). It comprises of one computing submodule (C1), one processing submodule (C2), one storage device (C3), one language and interactive tool (C4) that is a high-level language and interactive environment to run the processing submodule (C2) and one toolbox (C5) that is based on the language and interactive tool (C4) required for Image Processing (Ip) by the processing submodule (C2).

The processing submodule (C2) of the computation module (C) applies the technique of PET asymmetry after anatomical symmetrization coregistered to MRI (PASCOM) for analyzing and processing preprocessed PET (IPP) and MRI data (IMP) from storage and communication module (SC). It is configured with tools for analyzing and processing the Preprocessed PET (IPP) and MRI data, to include tools for segmentation, co-registration, registration, smoothing, quantitative analysis etc. The submodule performs analysis and processing of the preprocessed PET (IPP) and MRI (IMP) data using the technique of PET asymmetry after anatomical symmetrization coregistered to MRI (PASCOM) by steps such as but not limited to flipping, image segmentation, forward warping, inverse warping, finding asymmetry index, multiplying greyscale map, thresholding and clustering to obtain processed image that depicts the hypometabolic cerebral cortex for detection of Epileptogenic focus (EF).

The computation module (C) is configured with large capacity storage (C3) to handle the high data volumes generated by PET and MRI data of high-resolution and is equipped with fast processor (C6). The present invention provides an accurate and efficient technique that is independent of healthy control PET data and facilitates implementation and multicenter translation at affordable cost thereby assisting healthcare professionals in presurgical evaluation of pharmacoresistant epilepsy in subjects (Su).

The medical hardware system (A1) of acquisition module (A) is selected from systems that enable simultaneous acquiring of PET and MRI images of the subject (Su), such as but not limited to an integrated PET-MRI system with system platform such as syngo MR E11 Platform. The PET detector (A11) is a high-definition PET scanner with capacity for high-resolution imaging such as but not limited to PET scanner with Lutetium Oxyorthosilicate (LSO) crystals with effective detection of gamma rays and quick decay times.

The system provides for iterative reconstruction of the PET data with a multiple number of iterations and subsets. The PET detector (A11) comprises of one image reconstruction submodule (A111) for iterative reconstruction of PET data (IP) from the PET detector (A11) enhancing image quality and providing pre-processed PET data (IPP). The reconstruction of PET data is done in iterations in the range of 3-8 iterations preferably 5 and a plurality of subsets in the range of 15-30 preferably 21 subsets.

The MRI scanner (A12) of acquisition module (A) is capable of providing high-resolution magnetic resonance imaging such as but not limited to 3-Tesla MRI (3T MRI). The MRI Scanner (A12) is set for imaging protocols such as 3D FLAIR that is set with specific repetition time (TR), echo time (TE), inversion time (TI), matrix, and number of excitations and 3D MPRAGE that is a T1-weighted sequence providing high-resolution, isotropic 3D imaging of brain structures. The MRI scanner (A12) comprises of one MRI sequences tool (A121) for controlling parameters for MRI sequences from the MRI scanner (A12). This tool (A121) of MRI scanner (A12) controls parameters for MRI sequences such as 3D FLAIR and 3D T1-weighted MPRAGE, including timing (TR, TE, TI), field of view (FOV), matrix size, and number of excitations (NEX).

The pre-processed PET (IPP) and MRI data (IMP) and other associated data from medical hardware system (A1) is transferred to the storage and communication module (SC) via a secure hospital network using protocols. The storage and communication module (SC) has large-capacity storage (SC1) to handle high data volumes generated by high-resolution PET (IP) and MRI scans (IM). This module (SC) allows storage and remote accessibility of the PET (IPP) and MRI data (IMP) to computation module (C) for further processing.

As per an embodiment of the invention the language and interactive tool (C4) used is MATLAB R2017b or later version with toolbox (C5) that is based on the language and interactive tool (C4) such as SPM 12 toolbox. The tool for registration is a computing tool for image registration (C7) such as but not limited to DARTEL. The system (S) also utilizes a smoothing tool (C8) such as but not limited to 8-mm full width at half maximum (FWHM) Gaussian kernel.

The method for automatic detection of epileptogenic focus (EF) in subjects (Su) with pharmacoresistant epilepsy is described as follows. The data PET (IP) and MRI data (IM), from medical hardware system (A1) comprising of PET detector (A11) and MRI scanner (A12), of subjects (Su) or patients undergoing scanning interictally is acquired. The PET (IP) and MRI data (IM) on the medical hardware system (A1) with system processing software such as Syngo MR platform for basic image reconstructions is pre-processed to obtain pre-processed PET (IPP) and MRI data (IMP). The pre-processed PET (IPP) and MRI data (IMP) data and associated metadata from previous step are transferred to the storage and communication module (SC) that is integrated with medical hardware system (A1). The pre-processed PET (IPP) and MRI data (IMP) is stored in the storage and communication module (SC) and is available to be remotely accessed by the computation module (C). The pre-processed PET (IPP) and MRI data (IMP) to include FLAIR MRI image (IFM) and T1-weighted MRI image (ITM) from previous step from the storage and communication module (SC) is accessing remotely by a computation module (C). The pre-processed PET (IPP) and MRI data (IMP) from previous step undergoes in depth analysis and advanced processing such as advance image processing (Ip) by the computation module (C) that runs on a high-level language and interactive environment (C4). Thresholding and clustering of the smoothed AI images is performed thereby leading to automatic localizing and detection of epileptogenic focus (EF) in pharmacoresistant epilepsy subjects (Su).

The process of acquiring of PET and MRI data from medical hardware system (A1) for PET and MRI scanning of subjects (Su) interictally is performed by first preparing subjects (Su) by making them fast and maintaining euglycemia to ensure optimal uptake of radioactive tracer injection such as FDG for PET scanning. The subjects (Su) are made to rest in a specified environment to stabilize the baseline brain activity. The subjects (Su) are then administered FDG intravenously. Imaging is conducted using PET detector (A11) after one-hour of injecting the radioactive tracer injection. Simultaneous scanning using PET detector (A11) and MRI scanner in a single bed position is conducted for a 15-minute duration with specific sequences such as for MRI 3D FLAIR MRI, T1-weighted MRI (ITM) and settings tailored for brain imaging to obtain PET and MRI data.

Pre-processing step of the method utilizes processing tools for iterative reconstruction of PET data that are in the form of images thereby enhancing image quality by reducing noise and improving resolution. Transferring of data to storage and communication module (SC) was performed via a secure hospital network using protocols such as standard DICOM (Digital Imaging and Communications in Medicine) protocols.

The in depth analysis and processing such as advance image processing (Ip) by the computation module (C) is performed by first co-registering the pre-processed PET images (IPP) and MRI images (IMP) to include FLAIR MRI image (IFM) rigidly to the T1-weighted MRI image (ITM) to obtain co-registered images (IC). These co-registered images (IC) are flipped left to right while maintaining their anterior-posterior orientation to obtain flipped TI MRI (ITM1), flipped FLAIR MRI (IFM1) and flipped PET image (IPP1). Multispectral segmentation of the flipped MRI images (IFM1, ITM1) and un flipped MRI images is performed using T1-weighted MRI image (ITM) and FLAIR MRI (IFM) images to create grey and white matter probability maps (IG) with computing tool for image registration (C7) such as DARTEL import files through toolbox (C5) such as SPM12 for high level language and interactive tool (C4). An average symmetrical template (IT) using the computing tool for image registration (C7) such as DARTEL import files is created by nonlinear co-registration of the grey and white matter of flipped (IFM1, ITM1) and un flipped MRI (IFM, ITM) images. All images (IPP, ITM, IPP1, ITM1) are then warped to the average symmetrical template (IT) space created by computing tool for image registration (C7) using the corresponding flow fields of unflipped images by flow field 1 and flipped images by flow field 2. The warped images (IPPW, IPP1W, ITMW, ITM1W) thus obtained are thus corrected for interhemispheric structural asymmetry due to the precise overlap of anatomical regions on the flipped (IPP1, ITM1) and un flipped images (IPP, ITM). All the warped images (IPPW, IPP1W, ITMW, ITM1W) are then inversely warped using flow field 1. This causes warping of the un flipped images back to the native space and warping of the flipped images to anatomically overlap the grey and white matter of the un flipped images.

The inversely warped PET images are smoothed using Smoothing tool (C8) such as an 8-mm full width at half maximum (FWHM) Gaussian kernel to improve the signal-to-noise ratio. Asymmetry index (AI) image is calculated after inverse warping as per expression below:

$$AI=(\text{flipped}-\text{un flipped})/\max(\text{flipped},\text{un flipped})$$

wherein the difference between the flipped and un flipped PET images (flipped–un flipped) corresponds to the interhemispheric metabolic asymmetry.

To detect hypometabolism, the unflipped PET images (IPP) were subtracted from the flipped PET images (IPP1). Since different cortical regions have different uptake (e.g., lower in the insula and higher in the frontal lobe), the larger of two uptake values was taken in the denominator to normalize the absolute difference. Further the grey matter tissue probability map (IG) (Hadamard product) was multiplied to the AI image, restricting the analysis to the grey matter and these gray matter-restricted AI images were again smoothed using the 8-mm FWHM Gaussian kernel to obtain smoothed AI images.

The process of thresholding and clustering the smoothed AI images was carried out by converting the smoothed AI images to z-score AI images that were thresholded at $z>4$. The spatially clustered image Z4C was created Z4 by retaining the cluster of at least 100 voxels connected to the voxel with the peak AI value as shown in FIG. 4.

A retrospective pilot study was conducted to research and develop the system (S) and method of the present invention that included patient (Su) with drug-resistant epilepsy who had undergone PET-MRI for presurgical evaluation at the Amrita Advanced Centre for Epilepsy from 2015 to 2020. All patients included in this analysis had undergone resective surgery and had an Engel class I outcome for >12 months. Patient (Su) who had undergone callosotomy, hemispherectomy, or sub hemispheric disconnection were excluded from the study. This retrospective study was approved by the institutional ethics committee.

The interictal outpatient FDG-PET scans (IP) were acquired on a Siemens Biograph mMR system (high-definition PET with LSO crystal and 3-T MRI) using the latest syngo MR E11 platform. All patients fasted for 4 hours, were euglycemic before scanning, and rested in a quiet, darkened room with eyes open and ears unoccluded for 30 minutes before FDG administration and for at least 30 minutes afterward. Scanning commenced 1 hour after 0.1 mCi/kg body weight of FDG was injected intravenously. PET data were acquired for one bed position starting simultaneously with MRI for a duration of 15 minutes. Intravenous sedation was used for uncooperative patients. Whole-brain 3D FLAIR and 3D T1-weighted sequences were acquired with a 256-mm FOV and 1-mm isovolumetric voxel in the sagittal plane. 3D FLAIR scanning parameters included TR 5000 msec, TE 385 msec, TI 1800 msec, number of excitations (NEX) 1, and matrix 256×256. 3D MPRAGE T1-weighted scanning parameters were TR 2400 msec, TE 2.26 msec, TI 900 msec, NEX 1, and matrix 256×256 with an approximate scan time of about 6 minutes per sequence. Iterative reconstruction of PET data was done with 5 iterations and 21 subsets. Routine EEG monitoring was not performed during the scanning.

The presurgical and surgical details that are part of experimental studies for the development of present invention are as described in the following paragraph.

All subjects (Su) or patients underwent prolonged scalp video-EEG (VEEG), volumetric 3-T brain MRI, and FDG-PET studies. Interictal and ictal SPECT studies were done in a few patients (Su). An electroclinical hypothesis was generated from the VEEG data and then integrated with imaging data to formulate an anatomo-electroclinical hypothesis for the EZ/epileptic networks, and an intervention plan was formulated in the interdisciplinary patient management conference. Patient (Su) for whom intracranial EEG was decided on following multidisciplinary team discussion (MDT) underwent stereo-EEG (SEEG) electrode placement, long-term monitoring, and resection, as per the established protocols. Those undergoing direct single-stage epilepsy surgery underwent either standard anatomical anterior and mesiotemporal lobectomy via microsurgical technique or combined image- and electrocorticography (ECoG)-guided extratemporal resection of the epileptogenic lesions. Both SEEG electrode implantations and single-stage corticectomies were done by integrating routine FDG-PET data into robotic or navigation systems, but not the PASCOM data since these were retrospectively derived.

The PET scans (IPP) and FLAIR MRI (IFM) were rigidly co-registered to the T1-weighted MRI (ITM). These coregistered images were flipped left to right while maintaining their anterior-posterior orientation. Multispectral segmentation of flipped and unflipped MRI scans was done using T1-weighted and FLAIR images to create the gray and white matter probability maps along with the DARTEL import files through SPM12 in MATLAB version R2017b. These DARTEL import files were used to create an average Symmetrical template (IT) through nonlinear coregistration of the gray and white matter of flipped and unflipped MRI studies. All images were warped to the DARTEL-created template space using the corresponding flowfields of unflipped (flowfield 1) and flipped (flowfield 2) images, as shown in FIG. 3. In the average template space, the flipped and unflipped images had a precise overlap of anatomical regions and hence corrected the interhemispheric structural asymmetry. After that, all the warped images were inversely warped using flowfield 1. This step warped the unflipped images back to the native space, whereas the flipped images were warped to anatomically overlap the gray and white matter of the unflipped images. The inversely warped PET images were smoothed using an 8-mm full width at half maximum (FWHM) Gaussian kernel to improve the signal-to-noise ratio. After inverse warping, the AI image was calculated as follows: AI=(flipped−unflipped)/max(flipped, unflipped).

The difference between the flipped (IPP1) and unflipped PET images (IPP) corresponds to the interhemispheric metabolic asymmetry. To detect hypometabolism, the unflipped PET images (IPP) were subtracted from the flipped PET image (IPP1). Since different cortical regions have different uptake (e.g., lower in the insula and higher in the frontal lobe), the larger of two uptake values was taken in the denominator to normalize the absolute difference. Further, the gray matter tissue probability map was multiplied (Hadamard product) to the AI image, restricting the analysis to the gray matter. These gray matter-restricted AI images were again smoothed using the 8-mm FWHM Gaussian kernel.

The smoothed AI images were converted to z-score images. These z-score AI images were thresholded at z>3, z>4, and z>5 to create Z3, Z4, and Z5 images, respectively. The spatially clustered images Z3C, Z4C, and Z5C were created from Z3, Z4, and Z5 images, respectively, by retaining the cluster of at least 100 voxels connected to the voxel with the peak AI value as shown in FIG. 4. These AI images with different thresholds were compared with the region of resection to evaluate PASCOM's ability to detect focal hypometabolism related to the EZ on the FDG-PET images.

26 anatomical labels were defined in each hemisphere, as listed in Table 3, corresponding to 26 anatomical landmarks relevant to epilepsy surgery. These labels describe the regions detected on thresholded AI images and the resection cavity on postoperative MRI.

TABLE 3

Twenty-six anatomical labels defined on each hemisphere based on relevance to the epilepsy surgery

| Frontal Lobe | Temporal Lobe | Parietal Lobe | Occipital Lobe | Cingulate | Insula |
|---|---|---|---|---|---|
| Frontal pole | Lateral temporal neocortex | Precuneus | Cuneus | Anterior | |
| Orbitofrontal | Temporal pole | Primary sensory cortex | Lingual gyrus | Middle | |
| Superior frontal gyrus | Mesio-temporal | Inferior parietal lobule | Lateral occipital | Posterior | |
| Middle frontal gyrus | Posterior temporal | Superior parietal lobule | | | |
| Inferior frontal gyrus | Temporal operculum | Parietal operculum | | | |
| Premotor cortex | | | | | |
| Supplementary motor area | | | | | |
| Motor cortex | | | | | |
| Frontal operculum | | | | | |

FDG-PET images were visually analyzed in two phases. First, the images were analyzed by a nuclear medicine consultant blinded to the clinical data (VIS). Later, the images were visually analyzed by a nuclear medicine consultant and a neuroradiologist guided by the clinical revelations from other modalities during the MDT. The visual analysis results were also described using the predefined anatomical labels from Table 3

As all the patients (Su) had an Engel class I postsurgical outcome, the EZ was considered to reside within the resection cavity in these patients (Su). Hypometabolism detected by VIS and MDT and on Z3, Z3C, Z4, Z4C, Z5, and Z5C images was compared to the resection cavity using anatomical labels. The hypometabolic area concordant with the resection cavity was classified as the identified region (I), and the non-concordant area was classified as the non-resected region (NR) as shown in FIG. 5. The NR was subclassified as ipsilateral (NRI) and contralateral (NRC) if it was on the ipsilateral and contralateral side of the surgery, respectively. The label corresponding to the resection cavity not identified as hypometabolic was classified as the missed region (M).

The performance score (Sc) was defined as follows: $Sc=I/(M+NRI+2NRC+1)$. The score would improve with a greater number of identified regions (I) and would reduce with more missed regions (M) or hypometabolic regions not in resection (NR). Furthermore, NRC was arbitrarily multiplied by a factor of 2 to more heavily penalize any detection contralateral to the resection. The constant value of 1 was added to the denominator to provide a finite Sc value if M and NR were 0. The technique was considered lateralizing to the side of the EZ if it had nonzero I or NRI labels (i.e., nonzero AI only on the side of surgery).

The mean and standard deviation of Sc, I, M, and NR for each analysis technique were calculated. The sensitivity and specificity of each technique were also calculated for an individual patient considering I/52 as the true-positive rate, NR/52 as the false-positive rate, M/52 as the false-negative rate, and $1-[(I+M+NR)/52]$ as the true-negative rate, where 52 was the total number of labels in the brain. The paired two-tailed t-test for sensitivity, specificity, and S was performed for all possible pairs of techniques. Statistical analysis was performed using IBM SPSS version 20 (IBM Corp.), and the results were considered statistically significant for $p<0.05$.

Twenty-three patients (Su) fulfilled the study inclusion criteria and were analyzed. Thirteen males and 10 females had a mean age of 20.87±13.09 years. Preoperative MRI was abnormal in 16/23 patients (69.6%). All patient (Su) were seizure free for at least 12 months (mean 21.7±7.8 months) of follow-up after surgery. Hippocampal sclerosis was histopathologically found in 9 of 12 patients (Su) whose mesial temporal lobe had been resected. Also, of 14 patients (Su) with extratemporal lobe resection, 2 had reactive gliosis and 11 had focal cortical dysplasia. The demographic and clinical details of patient (Su) with MRI findings and histopathological examination reports are listed in Table 4. The postoperative MRJ studies recorded a mean of 10±4 months after surgery. A descriptive analysis is graphically presented in FIG. 6.

TABLE 4

Demographic and clinical details of study cohort

| Case | Age | | Age at Sz | Sz | | Scalp EEG | | Preop | | | | FU |
|---|---|---|---|---|---|---|---|---|---|---|---|---|
| No. | (yrs) | Sex | Onset | Frequency | Semiology | Interictal | Ictal | MRI | SEEG | Surgery | HPE | (mos) |
| 1 | 22 | M | 13 yrs | 1-2/mo | Lt T | Lt T | Lt T | + | Yes | Lt ATL & AH | HS | 12 |
| 2 | 3 | M | 14 mos | 20-25/day | NLL | NLL | NLL | – | No | Rt FL | NA | 13 |
| 3 | 43 | M | 1.5 yrs | 1-2/mo | Lt NL | Lt T | Lt T | + | No | Lt ATL & AH | HS | 15 |
| 4 | 26 | M | 16 yrs | 5/wk | Lt NL | Lt T | Lt T | + | No | Lt ATL & AH | HS | 20 |
| 5 | 7 | M | 9 mos | 1-2/day | NLL | NLL | NLL | + | No | Lt TL & AH & OF & POcc | FCD | 22 |
| 6 | 13 | M | 2 mos | 2-4/day | Lt F | Lt NL | Lt NL | + | No | Lt FL & ACG & SAH | HS, FCD | 19 |
| 7 | 21 | M | 9 yrs | 2-3/mo | Lt T | NLL | Lt NL | + | Yes | Lt ATL & AH | HS | 20 |
| 8 | 41 | F | 39 yrs | 2-3/day | Lt T | Lt T | Lt T | + | No | Lt ATL & AH | HS | 19 |
| 9 | 23 | M | 5 yrs | 1-2/wk | NLL | NLL | Bilat F | – | Yes | Rt FP | FCD | 25 |
| 10 | 24 | F | 8 yrs | 10-12/mo | Lt T | Bilat T | Lt TOcc | + | No | Lt LG & SH | RG | 24 |
| 11 | 10 | F | 3 mos | 1-2/wk | Rt F | NLL | Rt F | – | No | Rt SFG | FCD | 28 |
| 12 | 32 | M | 7 yrs | 5-15/mo | Rt F | Rt F, C, & T | Rt F | – | No | Rt MFG & SFG | FCD | 38 |
| 13 | 18 | F | 2 yrs | 0-1/yr | L PC | NLL | NLL | – | Yes | Rt MCG | FCD | 12 |
| 14 | 19 | F | 7 yrs | 2-3/wk | Rt T | Rt T | Rt T | + | No | Rt TL & AH | NA | 16 |
| 15 | 7 | M | 1 yr | 9-10/day | Lt NL | Lt F | Lt C | – | Yes | Lt SFG | FCD | 23 |
| 16 | 29 | F | 1 yr | 1/day | Lt F | Bilat T | Lt F | + | No | Lt OF & SFG & MFG | RG | 33 |
| 17 | 24 | F | 1.4 yrs | 3-4/day | NLL | Bilat C | Rt C | + | No | Rt PM & SMA | FCD | 34 |
| 18 | 14 | M | 6 mos | 1/mo | Lt PHR | Lt T & Bilat PHR | Lt PHR | + | Yes | Lt ATL & AH | HS | 24 |
| 19 | 5 | M | 2 yrs | 1-2/day | Bilat T | Bilat T | Lt T | – | Yes | Lt ATL & AH | HS | 12 |

TABLE 4-continued

Demographic and clinical details of study cohort

| Case No. | Age (yrs) | Sex | Age at Sz Onset | Sz Frequency | Semiology | Scalp EEG Interictal | Scalp EEG Ictal | Preop MRI | SEEG | Surgery | HPE | FU (mos) |
|---|---|---|---|---|---|---|---|---|---|---|---|---|
| 20 | 49 | F | 7 yrs | 4-5/mo | Rt T | Rt F & T | Rt T | + | No | Rt ATL & AH | HS | 27 |
| 21 | 11 | F | 2.3 yrs | 1-2/mo | Lt PHR | L PT | Lt PHR | + | No | Lt PO | FCD | 34 |
| 22 | 3 | M | 1.4 yrs | 3-4/day | Rt NL | Rt FC | Rt FC | + | No | Rt SFG | FCD | 17 |
| 23 | 36 | F | 20 yrs | Multiple/day | Rt NL | Rt C | Rt FC | + | No | Rt PM | FCD | 13 |

It was found that the mean Sc was maximum for Z4C (Sc=1.30±1.23), followed by Z4 (Sc=1.12±1.12), and was minimum for VIS (Sc=0.27±0.31). The sensitivity and specificity of the analysis techniques are shown in FIG. 7. Further, it was found that the mean I was maximum for MDT (I=2.57±2.41) and minimum for Z5C (I=1.39±1.03). Similarly, the mean M was maximum for Z5C (M=1.83±2.69) and minimum for MDT (M=0.65±1.61). Also, the mean labels identified as hypometabolic but not resected (NRI+NRC) were maximum for VIS, followed by MDT, and were minimum for Z5C.

A paired two-tailed t-test for Sc was performed and it was found that the pairwise difference was significant between VIS and all other analysis techniques except Z3 ($p<0.05$). Moreover, Z3 was not significantly different from both visual analysis techniques (VIS and MDT). Among all the described automated techniques, only Z4C, with the highest Sc, showed a significant difference from MDT ($p<0.05$). Also, the difference between Z4C and Z4 was not statistically significant.

It is observed that the automated technique of the present invention brings more standardization and mathematical precision to the analysis of PET than visual interpretation. MDT allows to establish whether the PET findings are concordant or discordant with all other presurgical variables to arrive at an effective management decision. Therefore, it is proven that the technique PASCOM of the present invention has the potential to replace visual interpretation. Therefore, the MDT can now focus on the PASCOM instead of the routine visual search for asymmetrical metabolism.

The study leading to the present study used the DARTEL tool to create the symmetrical anatomical template from individual MRI studies, thus fixing the problem of structural asymmetry as these avoid the misalignments by creating a Symmetrical template (IT) for each patient before analyzing the whole-brain PET.

In most of the patients (Su), the torcular herophili region as seen on T1-weighted MRI was frequently misclassified as gray matter during the segmentation step, as shown in FIG. 8A. DARTEL import files, when used to create a symmetrical template (IT), retained structural asymmetry in the torcular herophili region. In turn, the AI images acquired higher values in the torcular region that were likely to be detected as false positives. However, it was easy to distinguish between the torcular herophili region and cerebral gray matter on FLAIR MRI. Therefore, multispectral segmentation has been used to create the DARTEL import files. The segmentation would be aided with T1-weighted and FLAIR MRI information for better results (FIG. 8B).

The technique of the present invention was validated through the Engel class I postsurgical outcome. Unlike MRI, which does not require radioactive tracer injection, collecting age- and gender-matched normative PET data from healthy volunteers is difficult. Furthermore, the unavailability of age-matched normative PET data for pediatric epilepsy patients (Su) restricted the PET evaluation to visual analysis. The present invention analyzes the patient's (Su) PET data (10/23 pediatric epilepsy patient (Su)) independent of control data, making it more convenient for multicenter translation.

A performance score measure (Sc) was developed to critically evaluate the performance of the analysis techniques and select the thresholding parameters for PASCOM. The pairwise difference in Sc was statistically significant between VIS and all other analysis techniques except Z3 because the Sc in VIS and Z3 was inferior because of more NRC and NRI. These NRs were reduced either by clustering or by further increasing the threshold, improving the score value. However, the diminishing I and increasing M further reduced Sc for higher thresholds. I and NR were minimum in Z5C because of the more stringent threshold criterion, and for the same reason, M was maximum.

Sensitivity was highest in MDT and was significantly better than that in Z5 and Z5C by paired two-tailed t-test, whereas the sensitivity of all other threshold criteria was comparable to that in MDT. Therefore, Z5 and Z5C are not ideal threshold criteria because of their lower sensitivity. Z5C had maximum specificity, and the specificity of Z4C and Z5 was comparable to that of Z5C by paired 2-tailed t-test. Furthermore, Z3C and Z4C identified the side of epileptic focus correctly in all the patients. Additionally, Z4C had the highest Sc. Therefore, Z4C is recommended as an optimal threshold for lateralizing and localizing the EZ.

It is known in the state of the art that PET hypometabolism identifies the functional deficit zone, which is generally larger than the ictal-onset zone and often overestimates the required resection even if it has adequately localized the EZ. Therefore, PET data is routinely utilized for determining the margins of resection over and beyond the findings of intracranial EEG (either SEEG and/or acute ECoG) with or without anatomical borders of a lesion as defined on structural MRI. PET's utility lies more in localization of an epileptogenic focus (EF) where MRI fails. Therefore, the technique of the present invention primarily aids in localization of the EZ, especially in MRI-negative patient (Su).

EXAMPLES

The present invention shall now be explained with accompanying examples. These examples are non-limiting in nature and are provided only by way of representation. While certain language has been used to describe the disclosure, any limitations arising on account of the same are not intended. As would be seeming to a person skilled in the art, various working alterations may be made to the method in order to implement the inventive concept as taught herein. The figures and the preceding description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of steps of method or processes of data flow described herein may be changed and is not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

In an exemplary embodiment, the various components which together form the system (S) along with the working of the invention and the method thereof are illustrated below.

The hardware components that form part of the system (S) of the present invention and their details that form part of the system (S) are as enumerated below:

- Medical hardware system (A1) such as but not limited to Siemens Biograph mMR Scanner
  - Type: Integrated PET/MRI system.
  - PET Detector (A11): High-definition PET scanner with Lutetium Oxyorthosilicate (LSO) crystals known for their effective detection of gamma rays and quick decay times, making them ideal for high-resolution imaging.
  - MRI scanner (A12) system: 3-Tesla MRI, providing high-resolution magnetic resonance imaging.
  - Injection System: For intravenous administration of the radiotracer Fluorodeoxyglucose (FDG).
- Ancillary Equipment:
  - Patient bed: Moves into the scanner (motorized and adjustable).
  - Sedation equipment: For uncooperative patient (Su), including intravenous drip and monitoring equipment.
  - Environmental Control: Room setup to be quiet and darkened to maintain patient calmness.
- High-End Processing Computer:
  - Processor (C6): Equipped with a fast Core i7 processor.
  - RAM: 16 GB
  - Operating System: Windows platform As per an embodiment of the present invention the software components and their details that form part of the system are as enumerated below:

- System software/tool (A3) such as but not limited to Syngo MR E11 Platform:
  - Function of system software/tool (A3): The System software (A3) governs the operation of the MRI scanner, including the initiation of sequences, data acquisition parameters, and integration with the PET detector/scanner.
  - Image reconstruction: The System software (A3) utilizes algorithms for iterative reconstruction of PET images (5 iterations, 21 subsets), enhancing image quality by reducing noise and improving resolution.
  - MRI sequences software (A121): The MRI sequences software (A121) controls parameters for MRI sequences like 3D FLAIR and 3D T1-weighted MPRAGE, including timing (TR, TE, TI), field of view (FOV), matrix size, and number of excitations (NEX).
- Imaging Protocols:
  - 3D FLAIR: Set with specific repetition time (TR), echo time (TE), inversion time (TI), matrix, and number of excitations.
  - 3D MPRAGE: A T1-weighted sequence that provides high-resolution, isotropic 3D imaging of brain structures.
- Data Handling and Processing:
  - Storage: Large-capacity storage systems to handle the high data volumes generated by high-resolution PET and MRI scans.
  - Post-processing: Software tools for analyzing the PET and MRI data, which may include segmentation, co-registration, and quantitative analysis tools.
- Software for Data Analysis:
  - MATLAB R2017b: A high-level language and interactive environment to run the PASCOM processing.
  - SPM 12 toolbox: MATLAB based toolbox (C5) required for Image Processing (Ip) in PASCOM pipeline.

As per an embodiment of the present invention the process of data acquisition followed is as described below:

- Preparation: The subjects (Su) or patient are made to fast and maintain euglycemia to ensure optimal FDG uptake. They are made to rest in a specified environment to stabilize the baseline brain activity.
- FDG Administration: FDG dosed at 0.1 mCi/kg body weight, is injected intravenously to the subjects (Su) and the imaging commences one-hour post-injection.
- Scanning Protocol: Simultaneous PET and MRI scanning for the subjects (Su) is carried out in a single bed position for a 15-minute duration. PET and MRI data are acquired with specific sequences and settings tailored for brain imaging.

As per an embodiment of the present invention the process of data transfer to Storage and communication module (SC) such as but not limited to Picture archiving and communication system (PACS) and the details are as described below:

- Functionality: PACS is a medical imaging technology used primarily for storing, retrieving, presenting, and sharing images produced by various medical hardware modalities, such as PET and MRI scanners.
- Integration with imaging systems: After acquisition, PET and MRI data were initially processed on the scanner's own computing system.
- Network transfer: Images and associated data were transferred via a secure hospital network to the PACS. This system uses standard DICOM (Digital Imaging and Communications in Medicine) protocols.
- Data storage and accessibility: Once in PACS, the data could be accessed remotely by physicians and radiologists for review, further diagnostics, and long-term storage. The PASCOM computational unit assess the PET-MR data from PACS and produces post processing results.

The overall workflow of the method for automatic detection of Epileptogenic focus (EF) in pharmacoresistant epilepsy as per an embodiment of the present invention is described as below:

- Acquisition: PET and MRI data are acquired using the Siemens biograph mMR system, adhering to specific scanning protocols.

Initial Processing: Images are first processed on the syngo MR platform of Siemens biograph mMR system for basic reconstructions.

Data Transfer: The pre-processed images and associated metadata are transferred to PACS (SC) using DICOM standards over a secure network of the hospital.

Remote Access: The pre-processed PET-MR data were accessed through PACS (SC) for PASCOM post-processing.

Advanced Processing: Further in-depth analysis of the images was performed using the high-end computational unit running MATLAB, where PASCOM technique is applied for post-processing.

According to an embodiment of the present invention the preferred mode of working of the invention is brought out as below:

Image acquisition at acquisition module (A):

High resolution FDG PET (IP) must be acquired interictally.

Proper subject (Su)/patient preparation before scanning has to be done.

3T MRI (IM) must be acquired with a 256-mm FOV and 1-mm isovolumetric voxel in the sagittal plane.

3D FLAIR (IFM) scanning parameters: TR: 5000 msec, TE: 385 msec, TI: 1800 msec, number of excitations (NEX): 1, and matrix: 256×256.

3D MPRAGE T1 (ITM)-weighted scanning parameters: TR: 2400 msec, TE: 2.26 msec, TI: 900 msec, NEX: 1, and matrix: 256×256.

Iterative reconstruction of PET data (IP) with 5 iterations and 21 subsets is carried out.

Computational module (C) comprises of the following:

Computing submodule (C1): High end processing computer

Language and interactive tool (C4): MATLAB R2017b or later version with SPM 12 toolbox (C5)

Enough data storage (C3) to handle large data.

Advance (PASCOM) processing at processing submodule (C2):

PET images and MRI images must be co registered before advance (PASCOM) processing.

Precise thresholding of the resultant resulting (PASCOM) file i.e., z-score>4 followed by clustering the region of peak intensity.

We claim:

1. A method for detection of epileptogenic focus in subjects with pharmacoresistant epilepsy, comprising steps of:

acquiring PET and MRI data from a medical hardware system comprising a PET detector and an MRI scanner;

preprocessing said PET and MRI data on said medical hardware system with system processing tools;

transferring said pre-processed PET and MRI data and associated metadata to a storage and communication module integrated with the medical hardware system;

storing said pre-processed PET and MRI data to a computation module;

accessing said pre-processed PET and MRI data including a FLAIR MRI image and a TI-weighted MRI image from said storage and communication module by a computation module;

co-registering rigidly the pre-processed PET and MRI data including the FLAIR MRI image to the T1-weighted MRI image obtaining co-registered images;

flipping said co-registered images left to right while maintaining anterior-posterior orientation obtaining flipped T1-weighted MRI, flipped FLAIR MRI and flipped PET images;

performing multi spectral segmentation of the flipped T1-weighted MRI and the flipped FLAIR MRI images and the not flipped T1-weighted MRI and the not flipped FLAIR MRI images using the not flipped T1-weighted MRI and the not flipped FLAIR MRI images to create grey and white matter probability maps with the computing tool;

creating an average symmetrical template using said computing tool for image registration through nonlinear co-registration of the grey and white matter of the flipped and not flipped MRI images;

warping the flipped and not flipped PET and T1-weighted MRI images to the average symmetrical template using the corresponding flow fields of the not flipped PET and T1-weighted MRI images by flow field 1 and the flipped PET and T1-weighted MRI images by flow field 2 images thereby obtaining warped images corrected for interhemispheric structural asymmetry;

warping inversely the warped flipped and warped not flipped PET and T1-weighted MRI images using flow field 1 causing warping of the warped not flipped PET and T1-weighted MRI images back to the native space and warping of the warped flipped PET and T1-weighted MRI images to anatomically overlap the grey and white matter of the not flipped PET and T1-weighted MRI images;

smoothing said inversely warped PET images using a smoothing tool to improve the signal-to-noise ratio;

calculating an asymmetry index image after inverse warping as per expression: AI=(flipped−not flipped)/max (flipped, not flipped) wherein the difference between the inversely warped flipped and not flipped PET images corresponds to the interhemispheric metabolic asymmetry;

multiplying the grey matter tissue probability map to said AI image, restricting the analysis to the grey matter;

smoothing-the grey matter-restricted AI images a second time;

thresholding and clustering said smoothed AI images by converting said smoothed AI images to z-score AI images; and thresholding said z-score AI images at z>4, followed by clustering the region of peak intensity;

thereby localizing and detecting epileptogenic focus in the pharmacoresistant epilepsy subjects.

2. The method as claimed in claim 1, wherein said acquiring of PET and MRI data from the medical hardware system comprises steps of:

preparing subjects by making them fast and maintaining euglycemia to ensure optimal uptake of radioactive tracer injection;

ensuring said subjects rest in a specified environment to stabilize baseline brain activity;

administering FDG intravenously;

imaging using the PET detector after one-hour of injecting; and scanning simultaneously using the PET and MRI detectors in a single bed position for a 15-minute duration with specific sequences and settings tailored for brain imaging to obtain PET and MRI data.

3. The method as claimed in claim 1, wherein said pre-processing utilizes processing tools for iterative reconstruction of PET data that are in the form of images thereby enhancing image quality by reducing noise and improving resolution.

4. The method as claimed in claim 1, wherein said step of transferring data to storage and communication module is performed via a secure hospital network using standard DICOM (Digital Imaging and Communications in Medicine) protocols.

* * * * *